May 25, 1954 J. R. LODGE Plant Pat. 1,281
CAMELLIA PLANT
Filed June 4, 1953 2 Sheets-Sheet 1
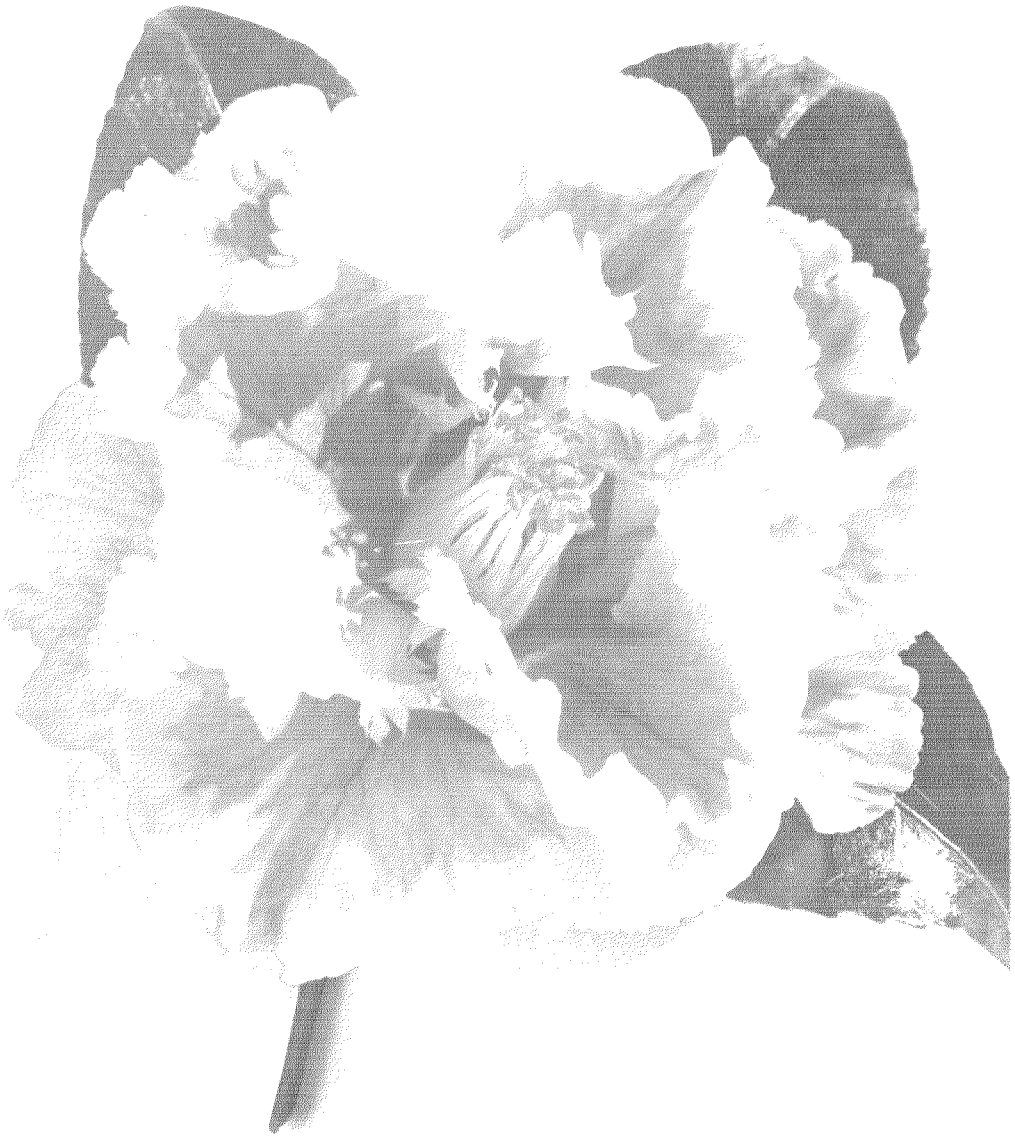
Inventor.
John R. Lodge
By: Robert Lobb
Attorneys CAMELLIA PLANT
Filed June 4, 1953 2 Sheets-Sheet 2
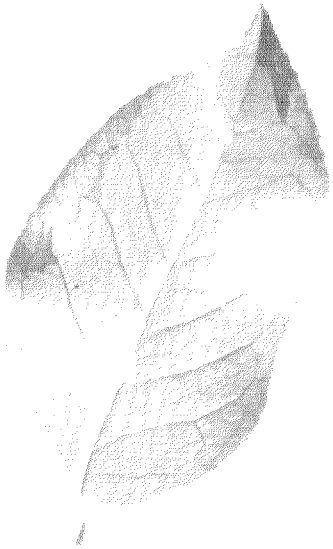
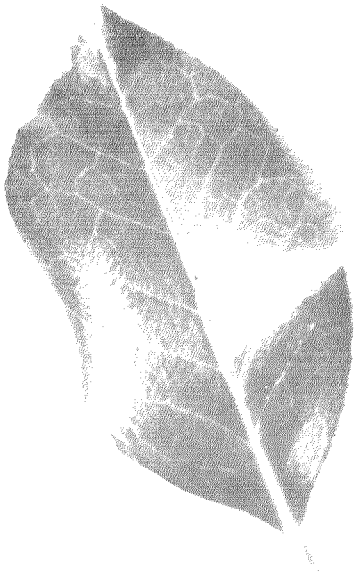
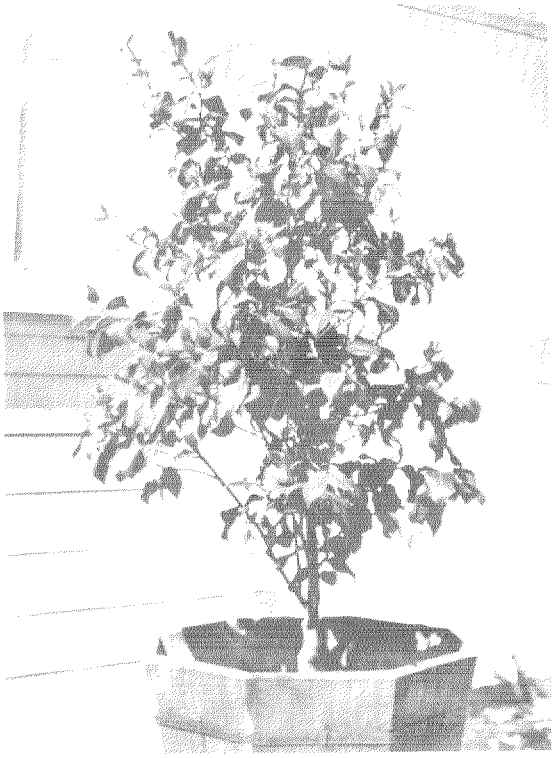
Inventor
John R. Lodge
By: Robb & Robb
Attorneys.

Patented May 25, 1954

Plant Pat. 1,281

UNITED STATES PATENT OFFICE 1,281

CAMELLIA PLANT

John R. Lodge, Altadena, Calif., assignor to Edward B. Arnesen, doing business as California Camellia Gardens, San Fernando, Calif.

Application June 4, 1953, Serial No. 359,677

1 Claim. (Cl. 47—60)

The present invention relates to a new and distinct variety of camellia plant originating as a sport of the unpatented variety "Fred Sander" (*Fimbriata superba*).

At the time of my discovery of the new sport, I was cultivating plants of the variety "Fred Sander" on my property at Altadena, California. Among these cultivated plants of the "Fred Sander" variety, my invention was attracted to one plant which bore flowers of a color that was definitely different and distinct from the normal color of the flowers of "Fred Sander." Upon closer examination of the plant, I found that the plant of "Fred Sander" had sported, whereupon, I promptly took steps to preserve the sport and asexually reproduced it to determine whether the new color characteristic of the sport was fixed and transmissible by asexual propagation. Such asexual propagation was performed by me by grafting at Altadena, California, and fully confirms that the new color characteristic of the sport is fixed and established, and is transmissible through succeeding propagations.

The parent variety "Fred Sander" (also known as *Fimbriata superba*) is considered to be one of the most unique and different camellias in existence, and is highly regarded and desired by both collectors and beginners who are interested in growing camellias, in addition to being very popular in general. Its flowers are solid crimson in color, are semi-double, and have curled, crepe-textured and fimbriated petals.

The new sport which is the subject of the present application is generally similar to the parent variety, having similar semi-double, curled, crepe-textured and fimbriated characteristics of its flowers, but the flowers of the sport variety are predominantly white in color, and have streaks and blotches of pink on each petal. Because of this difference in color of the flowers of my new variety, which is the principal difference, the crepe texture of the flowers, and the wavy and irregular outline of the flower petals, each of which is deeply notched and laciniated, are much more apparent than the corresponding characteristics in the flowers of "Fred Sander." The flower petals themselves in my new variety are prominently wrinkled and creased and retain the wrinkled appearance until the flower has matured and fallen from the plant.

Asexual reproduction of my new variety by grafting at Altadena, California, shows that the foregoing characteristics and distinctions come true to form and are established and transmitted through succeeding propagations. In addition to being definitely distinct from the parent variety "Fred Sander," my new variety of camellia is definitely distinguished from all other varieties of which I am aware, and none of which even approach the flower form, color, texture and petal intricacy of the new variety.

The accompanying drawings show typical specimens of the flowers and foliage of my new variety, one of said drawings being depicted in color and showing a fully-open mature flower, and the other drawing being depicted in black-and-white and showing a typical specimen plant and enlarged views of a typical specimen leaf as observed from the upper and lower sides thereof.

The following is a detailed description of my new variety, as based upon specimens grown and observed at Altadena, California, with color terminology in accordance with the Horticultural Chart issued by the British Color Council in collaboration with the Royal Horticultural Society, except where general color terms of ordinary dictionary significance are obvious:

Parentage: Sport of "Fred Sander."

*Flower*

Blooming Habit: Mid-season (February and March).

Bud:

*Size.*—Large.

*Form.*—Very long; pointed.

*Sepals.*—Smooth edge.

*Calyx.* — Shape — cupped. Size — large; broad. Color—Pod Green, Plate 061/2.

Bloom:

*Size.*—Medium-large; from 4 inches to 4½ inches.

*Borne.*—Singly, on strong, medium-long stems

*Form.*—When first petal opens—cupped; furled and wrinkled. When fully opened—irregular; rather cupped.

*Petalage.*—Semi-double; arranged irregularly.

*Color.*—Variegated — predominantly white, with streaks and blotches of Rose Madder, Plates 23/2 to 23/1.

Petals: Thick; soft; inside velvety; outside velvety; margins deeply laciniated and wrinkled.

*Arrangement.*—Irregular.

*Lasting quality.*—On plant—3 to 5 days. As cut flowers—3 to 5 days.

*Genital organs*

Stamens, anthers: Medium-small; 65 to 75 in number. Arrangement—cylindrical; fascicle of stamens subtended by 4 or 5 large petals and 1 or 2 small petals.

Stamens, filaments: Medium length; about ¾-inch. Color—Golden Yellow.

Pollen: Color—Golden.

Styles: Columnar; medium length; about ½-inch long. Color—Carmine Rose, Plate 621/1 at base, progressing from the tips from Carmine Rose, Plate 621/3, through Plates 621/2 and 621/1.

Ovaries: Enclosed in calyx; 4 or 5 stamens attached quite firmly to ovary.

Seeds: None have ever set.

*Plant*

Form: Bush shrub.

Growth: Medium vigor; compact.

Foliage:

*Size.*—Medium.

*Quantity.*—Normal.

*Color.*—Mature foliage: upper side—Spinach Green, Plate 0960; under side—Fern Green, Plate 0862/1. Young foliage: upper side—Lettuce Green, Plate 861; under side—Lettuce Green, Plate 861/1.

*Shape.*—Oval-pointed; undulated.

*Texture.*—Upper side—leathery; glossy. Under side.—smooth.

*Ribs and veins.*—Ordinary.

*Edge.*—Slightly serrated; undulated.

Wood:

*New wood.*—Color—Fern Green, Plate 0862/1.

*Firm wood.*—Color—Garnet Brown, Plate 00918.

I claim:

A new and distinct variety of camellia plant of the semi-double flower type, substantially as herein shown and described, characterized particularly as to novelty by the distinctive form and variegated color of its flowers, and by the petal intricacy and texture of its flowers, each flower being predominantly white in color, with blotches and streaks of pink therein, and the petals being crepe-textured, wavy and irregular in outline, with each petal deeply notched and laciniated, said petals retaining a wrinkled and creased appearance until the flower has matured and fallen from the plant.

No references cited.